United States Patent [19]

Groat et al.

[11] Patent Number: 4,533,544

[45] Date of Patent: Aug. 6, 1985

[54] METHOD OF FORMING STABLE DENTAL GEL OF STANNOUS FLUORIDE

[75] Inventors: Dennis E. Groat; Richard W. Sell, both of Dallas; Richard J. Kalish, Carrollton; Horace E. Melton, Irving, all of Tex.

[73] Assignee: Scherer Laboratories, Inc., Dallas, Tex.

[21] Appl. No.: 593,525

[22] Filed: Mar. 26, 1984

[51] Int. Cl.³ ..................... A61K 7/18; A61K 33/16
[52] U.S. Cl. ........................................ 424/52; 424/151
[58] Field of Search .................................. 424/52, 151

[56] References Cited

U.S. PATENT DOCUMENTS

| | | |
|---|---|---|
| 3,105,013 | 9/1963 | Saul et al. ............................ 424/52 |
| 3,282,792 | 11/1966 | Fiscella ................................. 424/52 |
| 3,337,412 | 8/1967 | Elbreder ............................... 424/151 |
| 3,892,843 | 7/1975 | Muhler et al. ........................ 424/52 |
| 3,929,988 | 12/1975 | Barth ..................................... 424/54 |
| 3,957,964 | 5/1976 | Grimm .................................. 424/49 |
| 4,071,615 | 1/1978 | Barth ..................................... 424/52 |
| 4,132,771 | 1/1979 | Schreiber et al. .................... 424/52 |
| 4,267,167 | 5/1981 | Weitzman et al. ................... 424/151 |
| 4,357,313 | 11/1982 | Harvey et al. ........................ 424/49 |
| 4,418,057 | 11/1983 | Groat et al. .......................... 424/151 |

*Primary Examiner*—Shep K. Rose
*Attorney, Agent, or Firm*—Emory L. Groff, Jr.

[57] ABSTRACT

A method of producing stable gels consisting essentially of from about 0.38% to about 0.42% of stannous fluoride, from about 0.25% to about 0.45% hydroxyethylallulose and the remainder anhydrous glycerin.

6 Claims, No Drawings

METHOD OF FORMING STABLE DENTAL GEL OF STANNOUS FLUORIDE

BACKGROUND OF THE INVENTION

Fluorides in a variety of forms have been demonstrated to be of significant value in reducing the occurrence of dental caries. Indeed, recognized authorities in the field of dental care have stated that there are "no bad fluorides" for this purpose.

Fluorides have been found to be best utilized for the prevention of caries when ingested, thus giving rise to the fluoridation of public water supplies. Fluorides are also of value when applied topically. A variety of topical fluoride treatments are provided professionally in the dental office. In addition, fluorides have been provided in commercial toothpastes and dentifrices. Of the fluorides available for topical application, stannous fluoride has proved to be the fluoride of choice due to the fact that the stannous ion combines with the naturally occurring phosphate in the enamel and dentin structures of the tooth to form stannous fluorophosphate which serves as a protective coating on the tooth surface.

Efforts have long been made by the leading commercial toothpaste marketers to make use of stannous fluoride as the source of "dentifrice-fluoride". Recently, however, the leading dentifrice producers have abandoned this effort, for various reasons which included the inherent instability of stannous fluoride in the presence of moisture and its reactivity with abrasives commonly used in dentifrices.

It is difficult, if not impossible, to avoid the exposure of the stannous fluoride to moisture and to the abrasives present in a dentifrice which have a negative effect on the stability of the stannous ion.

Thus, efforts have increased to make stannous fluoride available in a stable and efficacious form in applications other than in toothpaste and dentifrices. For the stannous ion to be of value it must be freely available and not in chemical combination with other ingredients as well as stable. Concentrations of stannous fluoride at a level of 0.1% available stannous ion have been demonstrated to be of value. A 0.4% stannous fluoride preparation has most frequently been demonstrated to be the concentration of choice in the treatment of dental caries.

While topical applications are frequently performed in the dental office there is also a need for follow-up daily application and use by the patient. Thus, "home-care" or "patient-care" availability is desirable. For this purpose a gel with the requisite viscosity to accommodate toothbrush application is the accepted marketable form.

Researchers recently discovered that stannous fluoride is relatively stable in anhydrous glycerin. However, glycerin solutions of stannous fluoride do not lend themselves to topical application to teeth because of their low viscosity. A variety of thickeners have been incorporated in glycerin solutions of stannous fluoride in an effort to increase the viscosity and, hence, the residence time of the composition on teeth when topically applied.

However, as in the case of dentifrices or toothpastes containing moisture and abrasives, the thickening agent used in preparing gels often contributes to the instability of the stannous fluoride. Not only is the choice of thickening agent critical to the stability of the available stannous ion, the technique in the process of making the gel product has been found to be of prime importance. In order to accommodate the demand for a "home-care" type gel, the product must be capable of being produced in quantities sufficiently large to make it economically feasible; i.e., "commercial-size-batches" from which smaller consummer-size packages may be formulated.

Thickeners such as sodium carboxy methyl cellulose react with stannous ion thus contributing to the instability of the product. Due to its non-ionic character, hydroxyethylcellulose has been suggested for use as a thickener. Careful preparation of a gel under rigorous laboratory conditions employing hydroxyethylcellulose has yielded stable preparations. Under such controlled conditions, factors which contribute to instability are easily kept at a minimum.

Attempts to prepare commercial-size batches of gel with hydroxyethylcellulose economically, however, have consistently met with failure. The processing, mixing, temperature, apparatus, etc., requirements of economically feasible large batch gel production techniques adversely affect the stability of the stannous ion/hydroxyethylcellulose/glycerin system.

In U.S. Pat. No. 4,418,057, owned by the same assignee, there is described a method for producing commercial-scale size batches of a stable gel containing stannous fluoride, glycerin and hydroxyethylcellulose which is stable over prolonged periods of time against deterioation. Briefly, the method described therein produces a commercial-scale size batch of stable gel consisting essentially of from about 96% to about 98% of anhydrous glycerin, from about 1.8% to about 2.2% of hydroxyethylcellulose and from about 0.38% to about 0.42% of stannous fluoride wherein the concentration of stannous fluoride in the gel is stable during storage under normal conditions against deterioration to levels below that desired in the use of the gel as a topical treating agent for the prevention of dental caries. The first stage of the method comprises the sequential steps:

(a) dissolving 50% of the stannous fluoride present in the gel in from about 15% to about 18% of the anhydrous glycerin present in the gel at a temperature in the range of from about 150° C. to about 185° C.;

(b) adding a sufficient quantity of anhydrous glycerin to the mixture to reduce the temperature thereof to from about 130° C. to about 150° C.;

(c) dissolving in the mixture 50% of the hydroxyethylcellulose present in the gel; and (d) adding to the mixture sufficient anhydrous glycerin to bring the volume thereof up to about 50% of the volume of gel; and the second stage of the method comprises repeating the sequential steps of the above first stage and combining the products of the two stages.

The invention described above was predicated on the discovery that preparing the gel according to the described procedure results in a formulation which is stable for long periods of time and at critical stability periods. Significant deviation from the protocol of the inventive method yields a product gel whose stannous fluoride concentration is rapidly reduced due to interaction with the hydroxyethylcellulose content thereof or from which the stannous fluoride will precipitate.

It is an object of the present invention to provide an improvement in the above-described method.

More particularly, it is an object of the present invention to provide a method for producing a stable commercial-size batch of gel containing stannous fluoride, glycerin and hydroxyethylcellulose wherein the amount of hydroxyethylcellulose in the gel is greatly reduced over that required in the above-described method.

SUMMARY OF THE INVENTION

The present invention provides a method of producing a commercial-scale size batch of a stable gel consisting essentially of from about 0.38% to about 0.42% of stannous fluoride, from about 0.25% to about 0.45% hydroxyethylcellulose wherein the concentration of stannous fluoride in the gel is stable during storage against deterioration to levels below that enabling the use of the gel as a topical treating agent for the prevention of dental caries. The method comprises the steps:

(a) dissolving the stannous fluoride present in the gel in from about 7.1% to about 7.2% of the glycerin present in the gel at a temperature in the range of from about 150° C. to about 180° C. to form a first stannous fluoride solution;

(b) admixing the first stannous fluoride solution with from about 23% to about 28% of the glycerin present in the gel at ambient temperature to form a second stannous fluoride solution;

(c) dissolving the hydroxyethylcellulose present in the gel in from about 33% to about 38% of the glycerin present in the gel at a temperature in the range of from about 130° C. to about 150° C.;

(d) intimately admixing the hydroxyethylcellulose solution with the second stannous fluoride solution; and (e) intimately admixing the resulting solution with the remainder of the glycerin present in said gel.

DETAILED DESCRIPTION OF THE INVENTION

As used herein, "commercial-batch-size" is meant to denote an amount that, when proportioned into packaged units, a sufficient number of units is yielded to make the process of manufacturing and packaging economically feasible for commercial distribution.

It should be noted that the determination of the "commercial-batch-size" must take into consideration factors other than economic factors, i.e., design of equipment; ability to control quality and consistency; ability to control environmental conditions (exposure to air and moisture); ability to control sensitive steps in the process (mixing times, cooling); ability to handle the process in safety; and the ability to maintain a balanced inventory of finished product so that a line of commercially attractive flavors and sizes can be made readily available.

The present invention enables a solution to this in that there is provided a method which (1) produces a composition which may be sub-divided and properly packaged for home-care use under professional supervision, (2) is of a viscosity so as to permit its use with a toothbrush as an applicator, and (3) is stable as to its stannous fluoride content over extended periods of time, particularly when stored under normal conditions. Further, the composition is of a quality and stability to equal the "laboratory produced compositions" used to clinically establish the efficacy and advantages of stannous fluoride topical fluoride treatment agents having known concentrations. Thus, the invention provides a commercially available composition in terms of quality and stability that will enhance the value of a variety of clinical studies such as (1) the further documentation of the value of stannous fluoride as a topical fluoride treatment for the purpose of reducing the occurrence of dental caries, (2) the further clinical documentation of the value of stannous fluoride in the area of hypersensitivity treatment, and (3) the further clinical documentation of the value of stannous fluoride in the area of plaque control.

The present inventive improvement of the earlier method of producing stable gels is predicated on the discovery that up to about an 80%, by weight, reduction in the amount of hydroxyethylcellulose needed for the gel may be achieved by following the above described method. Moreover, the reduction in the amount of hydroxyethylcellulose needed for the gel does not impair the desirable viscosity characteristics and stability of the gel. In addition, the time required to produce the commercial-scale-size batches has been greatly reduced owing to the fewer number of steps required for the improved method.

The apparatus described in U.S. Pat. No. 4,418,057, the disclosure of which is incorporated herein by reference, may also be employed to carry out the method of the present invention.

The percentages expressed herein are by weight and are based upon the weight of the final gel composition unless otherwise specified.

EXAMPLE 1

Preparation of Stannous Fluoride Solution

Glycerin (150 liters) was added to the tank and heated to 180° C. Stannous fluoride (17.2 kg) was added and the contents stirred until completely dissolved. The resulting solution was dissolved into a tank containing 61 liters of glycerin and the mixture mixed until homogeneous. The mixture may be stored in a tightly covered container indefinitely at temperatures no less than about 25° C.

EXAMPLE 2

Preparation of Flavored Gel

Glycerin (220 liters) was measured into a compounding tank. The glycerin was heated and hydroxyethylcellulose (2.6 kg) was added thereto with mixing. Heating was continued until the temperature reached about 140° C. The solution was mixed for 30 minutes at 140° C.

Glycerin (160 liters) was measured into a tank and 54 kg of the stannous fluoride solution of Example 1 added thereto. The hydroxyethylcellulose solution was added to the stannous fluoride solution with mixing until temperature equilibrium was reached.

One of the following batches of flavoring agent was intimately admixed with the solution; grape-2 kg; raspberry/creme de menthe-3.27 kg; cinnamon/creme de menthe-5.04 kg; mixed fruit-2.23 kg; mint-3.88 kg.

Finally, 225 kg of glycerin was added, thoroughly admixed therewith and the resulting gel packaged.

EXAMPLE 3

Preparation of non-Flavored Gel

Glycerin (100 liters) was added to a compounding tank and heated to 180° C. Stannous fluoride (3.0 kg) was added thereto and the solution mixed until completely dissolved (30 min.). An additional 100 liters of glycerin was admixed with the stannous fluoride solution.

Glycerin (150 liters) was measured into a compounding tank and hydroxyethylcellulose (2.6 kg) added thereto with mixing and heating to 140° C. until completely dissolved (30 min.).

The hydroxyethylcellulose solution was added to the stannous fluoride solution with mixing.

An additional 250 liters of glycerin was added and the resulting gel packaged.

We claim:

1. A method of producing a commercial-scale size batch of a stable gel consisting essentially of from about 0.38% to about 0.42% of stannous fluoride, from about 0.25% to about 0.45% hydroxyethylcelluose and the remainder anhydrous glycerin, wherein the concentration of stannous fluoride in said gel is stable during storage against deterioration to levels below that enabling the use of said gel as a topical treating agent for the prevention of dental caries, comprising the steps:

(a) dissolving the stannous fluoride present in said gel in from about 7.1% to about 7.2% of the anhydrous glycerin present in said gel at a temperature in the range of from about 150° C. to about 180° C. to form a first stannous fluoride;
 (b) admixing said first stannous fluoride solution with from about 23% to about 28% of the anhydrous glycerin present in said gel at ambient temperature to form a second stannous fluoride solution;
 (c) dissolving the hydroxyethylcellulose present in said gel in from about 33% to about 38% of the anhydrous glycerin present in said gel at a temperature in the range of from about 130° C. to about $\frac{1}{8}$° C.;
 (d) intimately admixing said hydroxyethylcelluose solution with said second stannous fluoride solution; and
 (e) intimately admixing said solution with the remainder of the anhydrous glycerin present in said gel.

2. The method of claim 1 wherein said steps (a) and (b) are carried out substantially simultaneously with step (c).

3. The method of claim 1 wherein said steps (a) through (e) are carried out sequentially.

4. The method of claim 1 including the step of adding at least one flavoring agent to either or both of the solutions produced according to steps (d) and (e).

5. The method of claim 1 including the step of packaging the said gel.

6. The gel produced according to the method of claim 1.

* * * * *